(12) United States Patent
Suga

(10) Patent No.: US 10,552,948 B2
(45) Date of Patent: Feb. 4, 2020

(54) ENDOSCOPE APPARATUS

(71) Applicant: OLYMPUS CORPORATION, Hachioji-shi, Tokyo (JP)

(72) Inventor: Takeshi Suga, Hino (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 16/171,232

(22) Filed: Oct. 25, 2018

(65) Prior Publication Data
US 2019/0066278 A1    Feb. 28, 2019

Related U.S. Application Data

(63) Continuation of application No. PCT/JP2017/019205, filed on May 23, 2017.

(30) Foreign Application Priority Data

Jun. 27, 2016   (JP) ................................ 2016-126629

(51) Int. Cl.
*G06T 5/00*     (2006.01)
*A61B 1/045*    (2006.01)
(Continued)

(52) U.S. Cl.
CPC .......... *G06T 5/006* (2013.01); *A61B 1/00193* (2013.01); *A61B 1/045* (2013.01);
(Continued)

(58) Field of Classification Search
CPC .................. G06T 5/006; G06T 2200/04; G06T 2207/10068; G06T 2207/20008;
(Continued)

(56) References Cited

U.S. PATENT DOCUMENTS

| 5,576,882 A * | 11/1996 | Kanamori | ............... A61B 1/002 359/362 |
| 2015/0062299 A1* | 3/2015 | Brown | .................... A61B 1/051 348/45 |
| 2015/0359422 A1* | 12/2015 | Igarashi | ............... G02B 23/243 600/135 |

FOREIGN PATENT DOCUMENTS

| JP | 08056891 A | 3/1996 |
| JP | 2003052057 A | 2/2003 |

(Continued)

OTHER PUBLICATIONS

International Preliminary Report on Patentability (IPRP) (and English language translation thereof) and Written Opinion dated Jan. 10, 2019 issued in International Application No. PCT/JP2017/019205.

(Continued)

*Primary Examiner* — Obafemi O Sosanya
(74) *Attorney, Agent, or Firm* — Holtz, Holtz & Volek PC

(57) ABSTRACT

An endoscope apparatus having a function of switching between the 2-D observation for a planar view and the 3-D observation for a stereoscopic view, includes an image Processor which carries out processing of reducing a distortion of an image pickup optical system for an image pickup signal achieved by an image pickup element of the endoscope apparatus at the time of the 3-D observation, and the image Processor carries out image processing that satisfies the following conditional expression (1):

$0.1 < B/A < 0.8$, as well as $A < 0$    (1)

where,
A denotes a distortion at the maximum image height at the time of the 2-D observation, and
B denotes a distortion at the maximum image height at the time of the 3-D observation.

4 Claims, 7 Drawing Sheets

(51) Int. Cl.
*A61B 1/00* (2006.01)
*H04N 5/357* (2011.01)
(52) U.S. Cl.
CPC ....... *H04N 5/3572* (2013.01); *G06T 2200/04* (2013.01); *G06T 2207/10068* (2013.01); *G06T 2207/20008* (2013.01); *G06T 2207/30004* (2013.01)
(58) Field of Classification Search
CPC . G06T 2207/30004; G06T 2207/10012; A61B 1/00193; A61B 1/045; A61B 1/00009; A61B 1/0005; A61B 1/00; H04N 5/3572; H04N 5/232; G02B 23/243; G02B 23/2415
See application file for complete search history.

(56) References Cited

FOREIGN PATENT DOCUMENTS

JP 5818265 B2 11/2015
JP 2015220643 A 12/2015

OTHER PUBLICATIONS

International Search Report (ISR) dated Jul. 18, 2017 issued in International Application No. PCT/JP2017/019205.
Written Opinion dated Jul. 18, 2017 issued in International Application No. PCT/JP2017/019205.

* cited by examiner

ENDOSCOPE APPARATUS

CROSS-REFERENCE TO RELATED APPLICATION

The present application is a continuation application of PCT/JP2017/019205 filed on May 23, 2017 which is based upon and claims the benefit of priority from Japanese Patent Application No. 2016-126629 filed on Jun. 27, 2016; the entire contents of which are incorporated herein by reference.

BACKGROUND OF THE INVENTION

Field of the Invention

The present invention relates to an endoscope apparatus.

Description of the Related Art

Endoscope is an instrument that has been used widely in a medical field and an industrial field. In the medical field, images of various parts inside a body cavity are achieved by an endoscope inserted inside the body cavity. Diagnosis (screening and close examination) of a part observed is carried out by using these images. In such manner, endoscope is used for diagnosis (screening and close examination) of various parts inside the body cavity, and treatment.

In the observation by an endoscope, a plurality of images having a parallax is picked up, and accordingly, a stereoscopic display (3-D (3-dimensional) display) of an image by fusing the plurality of images is carried out.

Such endoscope apparatuses which enable to switch between a 3-D observation having a stereoscopic effect and a 2-D (2-dimensional) observation for a planar view have been proposed in Japanese Patent Application Laid-open Publication No. 2015-220643 and Japanese Patent Publication No. 5818265.

Moreover, in the 3-D observation, a stereoscopic image pickup system which carries out distortion correction has been proposed in Japanese Patent Application Laid-open Publication No. 2003-52057.

SUMMARY OF THE INVENTION

An endoscope apparatus according at least some embodiments of the present invention, having a function of switching between a 2-D observation for a planar view and a 3-D observation for a stereoscopic view, includes an image Processor which carries out processing of reducing a distortion of an image pickup optical system for an image pickup signal achieved by an image pickup element of the endoscope apparatus at the time of the 3-D observation, wherein the image Processor carries out image processing that satisfies the following conditional expression (1):

$$0.1 < B/A < 0.8, \text{ as well as } A < 0 \quad (1)$$

where,

A denotes a distortion at the maximum image height at the time of the 2-D observation, and B denotes a distortion at the maximum image height at the time of the 3-D observation.

DETAILED DESCRIPTION OF THE INVENTION

An endoscope apparatus according to an embodiment will be described below in detail by referring to the accompanying diagrams. However, the present invention is not restricted to the embodiments and the examples described below.

Figure 1:
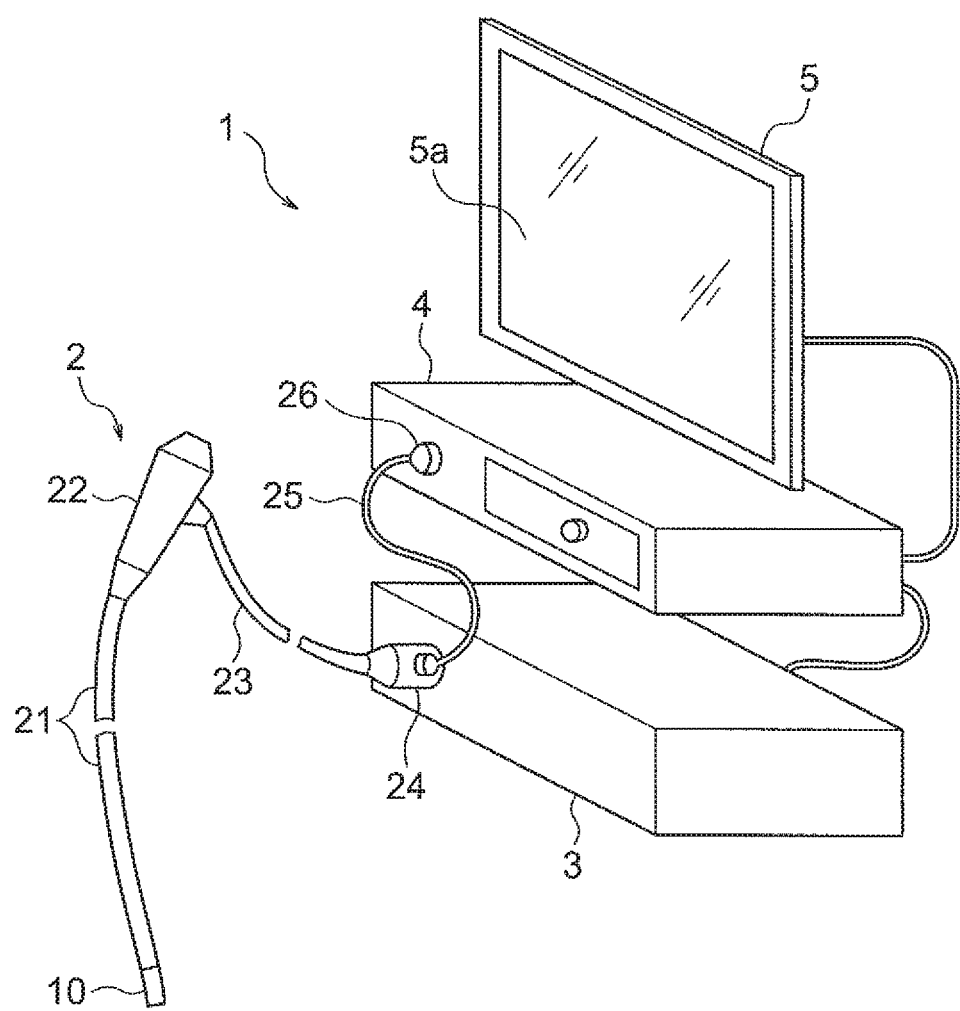
FIG. 1 is a diagram showing a schematic arrangement of an endoscope apparatus according to an embodiment of the present invention.

FIG. 1 is a diagram showing a schematic arrangement of an endoscope apparatus 1 according to the present embodiment. As shown in FIG. 1, the endoscope apparatus 1 of the present embodiment includes an electronic endoscope 2 having an image pickup element 12 (refer to FIG. 2) built-in, as an image pickup apparatus, a light-source unit 3 having a light source that supplies illumination light to the electronic endoscope 2, an image processing section 4 which carries out signal processing on the image pickup element 12 of the electronic endoscope 2, and a monitor 5 which displays an endoscope image by a video signal output via the image processing section 4. For example, the image processing section 4 is an image processor. The image processing section 4 includes a plurality of electronic circuits.

The electronic endoscope 2 includes an insertion portion 21 which is long, slender, and flexible, and in which the image pickup element 12 is built-in, an operating section 22 having a thick width and formed at a rear end of the insertion portion 21, a rigid tip portion 10, and a universal cord 23 which is extended from a side portion of the operating section 22. An end portion of the universal cord 23 is provided with connector 24 which is detachably connectable to the light-source unit 3. An end portion of a connecting cord 25 extended toward the connector 24 is provided with an electric connector 26 which is detachably connectable to the image processing section 4.

Figure 2:
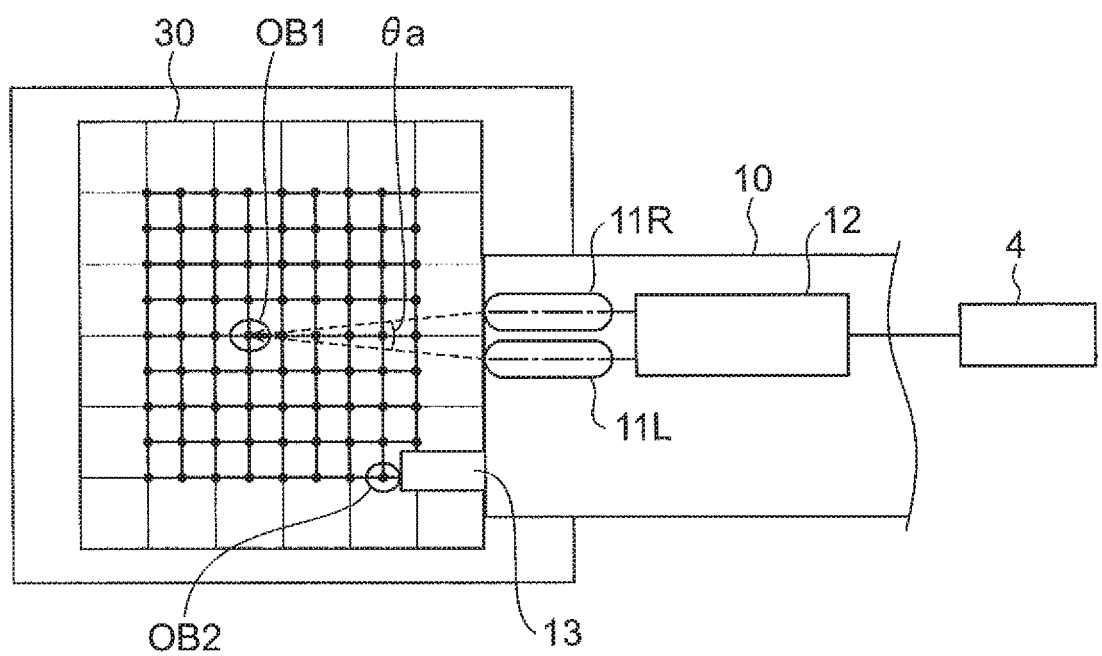
FIG. 2 is a diagram illustrating an object space of the endoscope apparatus according to the present embodiment.

FIG. 2 is a diagram illustrating an object space of the endoscope apparatus 1 according to the embodiment. The endoscope apparatus 1 of the present embodiment has two optical systems which are, an optical system for the right eye 11R and an optical system for the left eye 11L. An arrangement in detail of the two optical systems will be described later.

In the object space 30, a right-eye image and a left-eye image of an object OB1 is formed on an image pickup surface by the optical system for the right eye 11R and the optical system for the left eye 11L respectively. The image processing section 4 performs image processing that will be described later, on an output signal from the image pickup element 12. Thereafter, the image processing section 4 outputs a signal for an image for the right eye and a signal for an image for the left eye subjected to image processing, to the monitor 5.

In FIG. 2, an angle θa made by a straight line connecting a point at which an optical axis of the optical system for the right eye 11R and a lens surface nearest to object intersect and the object OB1, and a straight line connecting a point at which an optical axis of the optical system for the left eye 11L and the lens surface nearest to object intersect and the object OB1, is let to be an inward angle.

Figure 3:
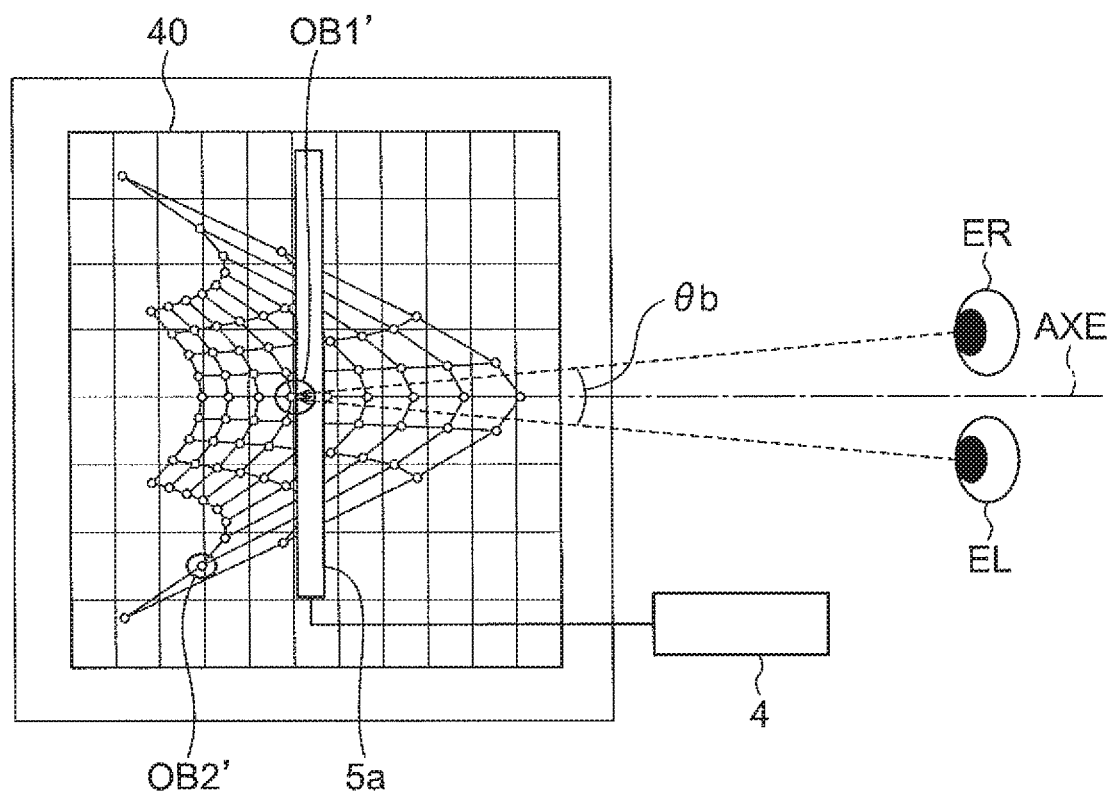
FIG. 3 is a diagram illustrating a reproducing space of the endoscope apparatus according to the present embodiment.

FIG. 3 is a diagram illustrating reproducing an object image OB1' in the present embodiment. In a reproducing space 40, an image for the right eye and an image for the left eye are displayed on a monitor surface 5a of the monitor 5, on the basis of a signal from the image processing section 4.

FIG. 3 shows a case in which the object image OB1' is displayed on the monitor surface 5a of the monitor 5. An angle θb made by a straight line connecting a line of sight of a right eye ER of an observer and the object image OB1' and a straight line connecting a line of sight of a left eye EL and the object image OB1' is let to be an angle of convergence.

As it is evident upon comparing FIG. 2 and FIG. 3, even when a flat object is observed, in the 3-D observation, a central portion is projected out frontward to be convex, and a peripheral portion is seemed to have receded toward an inner side. For instance, an object OB2 of the peripheral portion is reproduced at an inner side of the monitor surface 5a as an object image OB2' displayed at a periphery of the monitor surface 5a.

The endoscope apparatus 1, in an endoscope apparatus having a function of switching between the 2-D observation for a planar view and the 3-D observation for a stereoscopic view, has the image processing section 4 which reduces a distortion of an image pickup optical system at the time of the 3-D observation, and the image processing section 4 carries out image processing that satisfies the following conditional expression (1):

$$0.1 < B/A < 0.8, \text{ as well as } A < 0 \tag{1}$$

where,

A denotes a distortion at the maximum image height at the time of the 2-D observation, and B denotes a distortion at the maximum image height at the time of the 3-D observation.

Here, an endoscope apparatus intended for observing organs such as digestive organs, bronchial tube, and bladder is used for screening, close examination, and treatment.

Figure 4:
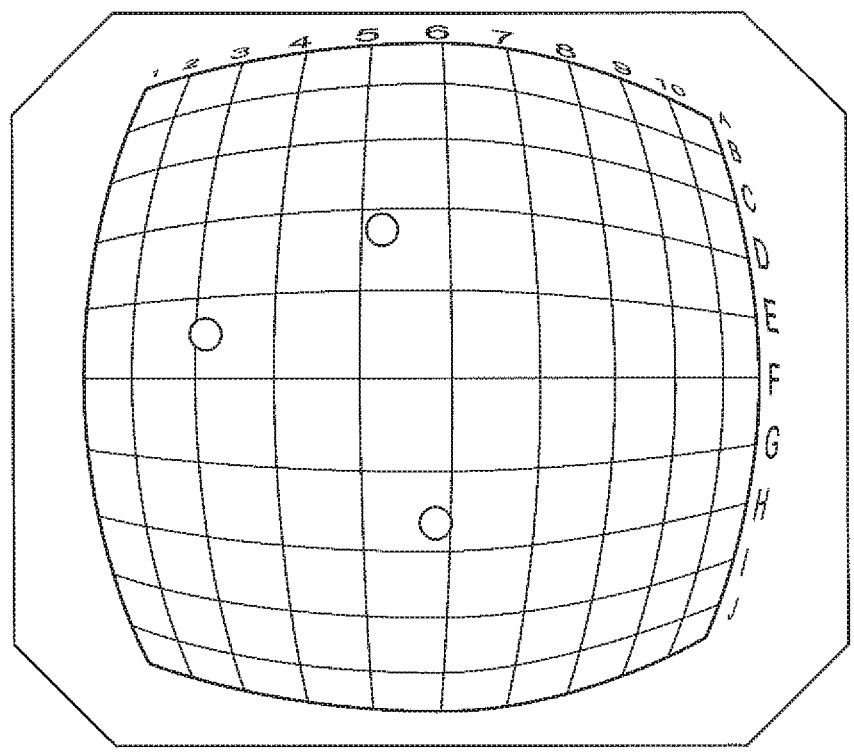
FIG. 4 is a diagram showing an observation image in a state of not being corrected when a square lattice was let to be an object.

FIG. 4 is a diagram showing an observation image in a state of not being corrected when a square lattice was let to be an object. In the screening, in a visual field of a wide angle of view, it is important not to overlook a lesion part. For this, as shown in FIG. 4, it is a common practice to use an optical system having a large negative distortion. Moreover, since there are cases in which an object distance becomes long in the screening, sometimes an adequate stereoscopic effect cannot be achieved in the 3-D observation. Therefore, in a wide angle 2-D observation in screening, it is necessary to observe a wide-angle range.

Next, in the close examination and treatment, since a lesion part is observed closely, the required stereoscopic effect is achieved. Therefore, it is necessary to make an arrangement such that the 3-D observation can be used. However, when the 3-D observation is carried out for an image of an optical system having a large negative distortion, as shown in FIG. 2 and FIG. 3, a 3-D reproducing space is deformed, and there is a shift in display of depth, and moreover, a vertical shift occurs at a periphery of the image, the observer may feel the fatigue.

Therefore, in the present embodiment, in the image processing section 4, the distortion of the optical system (FIG. 4) is reduced by image processing at the time of the 3-D observation. The image processing section 4 executes the image processing that satisfies the following conditional expression (1):

$$0.1 < B/A < 0.8, \text{ as well as } A < 0 \tag{1}$$

where,

A denotes a distortion at the maximum image height at the time of the 2-D observation, and B denotes a distortion at the maximum image height at the time of the 3-D observation.

By a value falling below an upper limit value of conditional expression (1), it is possible to prevent the shift in the display of depth, and moreover, the vertical shift at the periphery of the image is reduced, thereby enabling to reduce the fatigue of the observer.

By exceeding a lower limit value of conditional expression (1), an arrangement is made such that a small amount of the negative distortion is left. Accordingly, since it becomes easy to secure the visual field of a wide angle of view, as well as to make an amount of correction small, it is possible to minimize degradation of an image quality in a peripheral portion due to image processing. Moreover, it is possible to reproduce a treatment tool 13 that is inserted into and drawn out from a front-end portion of the endoscope (refer to FIG. 2), at an inner side of the monitor 5. Therefore, the observer does not have to become cross-eyed, and it is possible to reduce fatigue. For instance, when the negative distortion is corrected entirely, since deformation of the 3-D reproducing space is ceased, a position at which the treatment tool is reproduced becomes frontward of the monitor 5, and causes fatigue. In the present embodiment, by leaving the negative distortion by small amount, this problem is avoided.

Moreover, according to a preferable aspect of the present embodiment, it is desirable that the following conditional expression (2) be satisfied:

$$0.6 < D/C \leq 1 \text{ as well as } 100 \text{ degrees} < C \tag{2}$$

where,

C denotes the maximum angle of view at the time of the 2-D observation, and

D denotes the maximum angle of view at the time of the 3-D observation.

By a value falling below an upper limit value of conditional expression (2), an angle of view of the 3-D observation is set to be narrow, and an amount of distortion of the optical system is reduced. Accordingly, it is possible to make small the amount of correction by image processing, and to minimize the degradation of the image quality at the peripheral portion due to the image processing.

By exceeding a lower limit value of conditional expression (2), it is possible to secure a visual field range necessary for the 3-D observation.

Moreover, according to a preferable aspect of the present embodiment, it is desirable that the image processing section 4 reduce the distortion according to the following conditional expression (3):

$$Y = E \times X^3 + F \times X^2 + G \times X + H \tag{3}$$

where, for the maximum value of X, 0.4 < Y < 0.8,

X denotes an image height before image processing,

Y denotes (the image height before image processing)/(an image height after image processing), and E, F, G, and H denote coefficients.

By letting the parameter Y to be not more than 0.8, it is possible to reduce the shift in the display of depth and to reduce the fatigue of the observer.

By letting a lower limit value of parameter Y to be not less than 0.4, the degradation of the image quality at the peripheral portion due to image processing is minimized, and is kept at a level acceptable by the observer. In other words, an image is enlarged in a peripheral direction from an image center by image processing, and the farther the image peripheral portion from the center, larger is the amount of enlargement. Therefore, since the image is enlarged substantially at the image peripheral portion, the observer visually perceives the image to be blurred. Moreover, since an image noise is extended only in the peripheral direction, the noise becomes elliptical-shaped, and the image quality is degraded. In the present embodiment, measures are taken to solve these issues.

Moreover, according to a preferable aspect of the present embodiment, it is desirable that the following conditional expression (4) be satisfied:

$$-0.7 < B < -0.1 \quad (4)$$

where,

B denotes the distortion of the maximum image height at the time of the 3-D observation.

By exceeding a lower limit value of conditional expression (4), it is possible to make an arrangement such that there is no shift in the display of depth, and also to reduce the vertical shift in the image periphery, and to reduce the observer's fatigue.

By a value falling below an upper limit value of conditional expression (4), it is possible to secure an image quality of the visual field range and the peripheral portion. Moreover, it is possible to reproduce the treatment tool 13 that is inserted into and drawn out from the front-end portion of the endoscope, at an inner side of the monitor 5. Therefore, the observer does not have to become cross-eyed, and it is possible to reduce fatigue.

(Objective Optical System)

To begin with, an objective optical system common for examples from an example 1 to an example 5 to be described later will be described below.

Figure 9:
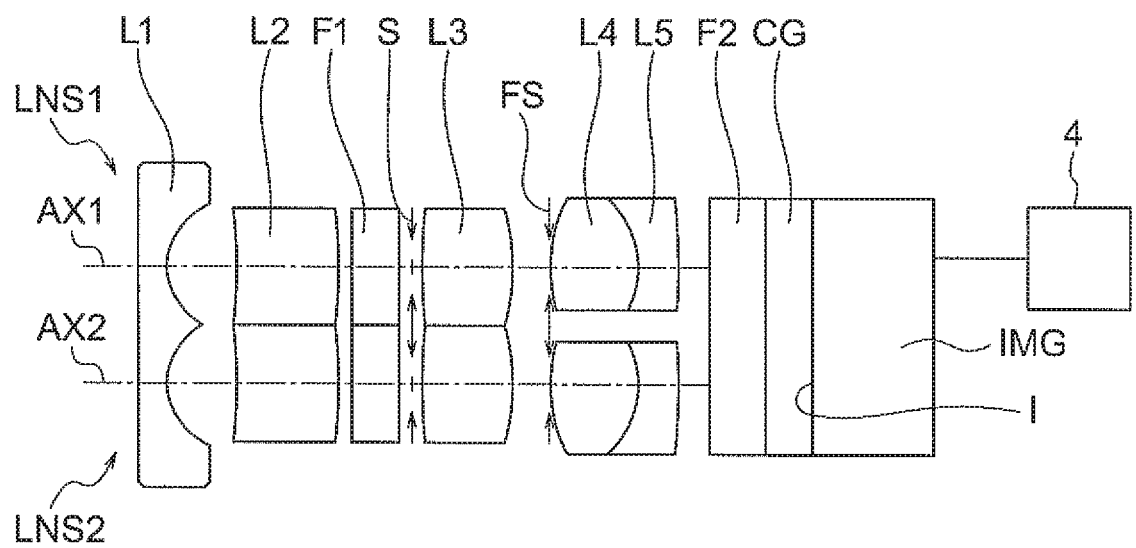
FIG. 9 is a diagram showing a schematic arrangement of an endoscope apparatus according to an example.
Figure 10:
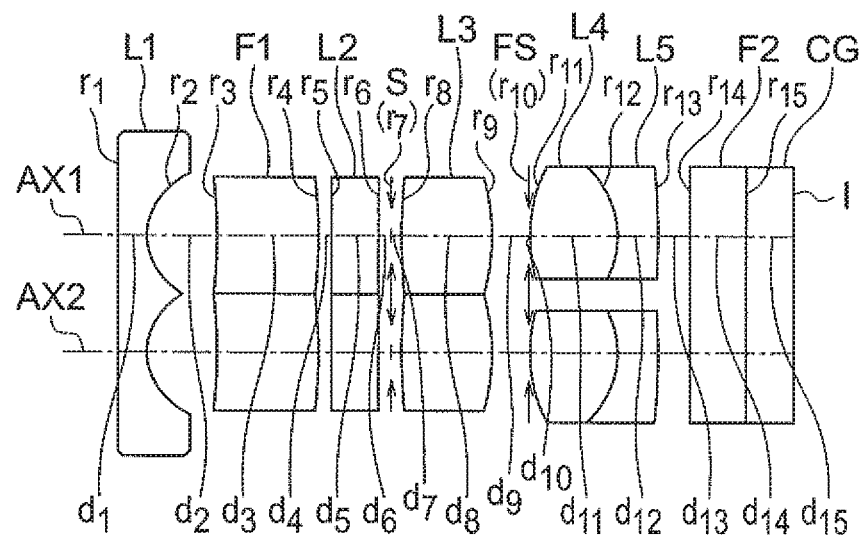
FIG. 10 is a cross-sectional view showing a lens arrangement of the endoscope apparatus according to the example.

FIG. 9 is a diagram showing a schematic arrangement of an endoscope apparatus according to an example. FIG. 10 is a cross-sectional view showing a lens arrangement of the endoscope according to the embodiment.

As shown in FIG. 9 and FIG. 10, the present example has a first optical system LNS1 and a second optical system LNS2, which generate two optical images having a parallax mutually. Each optical system includes in order from an object side, a planoconcave negative lens L1 having a concave surface directed toward an image side, a positive meniscus lens L2 having a convex surface directed toward the image side, a plane parallel plate F1, an aperture stop S, a biconvex positive lens L3, a flare aperture FS, a biconvex positive lens L4, a negative meniscus lens L5 having a convex surface directed toward the image side, a plane parallel plate F2, a plane parallel plate CG, and an image pickup element IMG. Moreover, AX1 and AX2 are respective optical axes of the two optical systems.

The first lens L1 is formed by an integral member for the first optical system LNS1 (subordinate optical system for example) and the second optical system LNS2 (main optical system for example). The positive lens L4 and the negative meniscus lens L5 are cemented. The plane parallel plate F2, the plane parallel plate CG, and the image pickup element IMG are cemented. Moreover, I is an image plane (image pickup surface).

A lens arrangement of the first optical system LNS1 and a lens arrangement and the second optical system LNS2 are the same.

Numerical data for the present example is shown below. Regarding symbols, r denotes a radius of curvature of each lens surface, d denotes a distance between two lens surfaces, nd denotes a refractive index of each lens for a d-line, and vd denotes Abbe number for each lens. Moreover, S denotes an aperture stop and FS denotes a flare aperture.

EXAMPLE 1

| Unit mm | | | | |
|---|---|---|---|---|
| Surface data | | | | |
| Surface no. | r | d | nd | vd |
| 1 | ∞ | 0.2500 | 1.88815 | 40.76 |
| 2 | 0.5920 | 0.5700 | | |
| 3 | −4.5711 | 0.8554 | 1.85504 | 23.78 |
| 4 | −3.3786 | 0.1100 | | |
| 5 | ∞ | 0.4000 | 1.49557 | 75.00 |
| 6 | ∞ | 0.1000 | | |
| 7 (Stop) | ∞ | 0.1016 | | |
| 8 | 7.9475 | 0.7436 | 1.83932 | 37.16 |
| 9 | −1.8802 | 0.3135 | | |
| 10 (FS) | ∞ | 0.0000 | | |
| 11 | 1.3149 | 0.7438 | 1.69979 | 55.53 |
| 12 | −0.8298 | 0.3347 | 1.93429 | 18.90 |
| 13 | −5.6819 | 0.2635 | | |
| 14 | ∞ | 0.5000 | 1.51825 | 64.14 |
| 15 | ∞ | 0.3500 | 1.50700 | 63.26 |
| Image pickup surface | ∞ | | | | focal length of the entire system f1 0.4249
parallax 1 mm
The example 1 to the example 5 of an image pickup apparatus will be described below. The abovementioned objective optical system is used in common in the five examples described below.
Contents of correction formula
Correction formula Y
Examples 1, 2
A Y = −1.1583X$^3$ − 1.1544X$^2$ − 0.0069X + 1.0021
Examples 3, 4, 5
B Y = −5.1946X$^3$ − 0.186X$^2$ − 0.2106X + 1.0081

Values for each example are shown below. Here, DT denotes a distortion. The unit of an image height is mm.

| | DT 2-D observation A | DT 3-D observation (after correction) B | DT B/A |
|---|---|---|---|
| Example 1 | −84.8% | −45.7% | 0.54 |
| Example 2 | −84.8% | −62.3% | 0.73 |
| Example 3 | −84.8% | −10.0% | 0.12 |
| Example 4 | −84.8% | −28.6% | 0.34 |
| Example 5 | −84.8% | −67.1% | 0.79 |

| | Angle (°) 2-D observation C | Angle (°) 3-D observation D | Angle (°) 3-D observation D/C | Correction formula Y |
|---|---|---|---|---|
| Example 1 | 163.7 | 134.9 | 0.82 | A |
| Example 2 | 163.7 | 150.8 | 0.92 | A |
| Example 3 | 163.7 | 99.98 | 0.61 | B |
| Example 4 | 163.7 | 134.9 | 0.82 | B |
| Example 5 | 163.7 | 163.7 | 1.00 | B |

-continued

| | Unit mm | | |
|---|---|---|---|
| | Calculation data | | |
| | 2-D observation image height | 3-D observation image height before correction | 3-D observation image height after correction |
| Example 1 | 0.43 | 0.4 | 0.54 |
| Example 2 | 0.43 | 0.42 | 0.593 |
| Example 3 | 0.43 | 0.33 | 0.45 |
| Example 4 | 0.43 | 0.4 | 0.71 |
| Example 5 | 0.43 | 0.43 | 0.93 |

| | 3-D observation image height reverse magnification Y | 3-D observation DT before correction H | 3-D observation angle of view before correction |
|---|---|---|---|
| Example 1 | 0.7407407 | −59.80% | 134.9 |
| Example 2 | 0.7082631 | −73.30% | 150.8 |
| Example 3 | 0.7333333 | −34.00% | 99.98 |
| Example 4 | 0.5633803 | −59.80% | 134.9 |
| Example 5 | 0.4623656 | −84.80 | 163.7 |

A formula for calculating a distortion (DT) value B for the 3-D observation is shown below.

A distortion definition before DT correction $$(|I'|-|\beta \times I|)/|\beta \times I|=H \quad (AA)$$

where,
I denotes an object height at an object surface,
I' denotes an image height at an image pickup surface (CCD (charge coupled device) surface), and
β denotes a lateral magnification when the object (object height I) was captured.

Moreover, a distortion definition after the DT correction is shown below.

$$(|I'/Y|-|\beta \times I|)/|\beta \times I|=B \quad (BB)$$

where,
I denotes the object height at the object surface,
I' denotes the image height at the image pickup surface (CCD surface),
β denotes the lateral magnification when the object (object height I) was captured, and
Y is image height before correction/image height after correction Moreover, the following expression is achieved from expressions (AA) and (BB).

$$|I'|=(H+1) \times |\beta \times I|$$

$$B=(H+1)/Y-1$$

Figure 5:
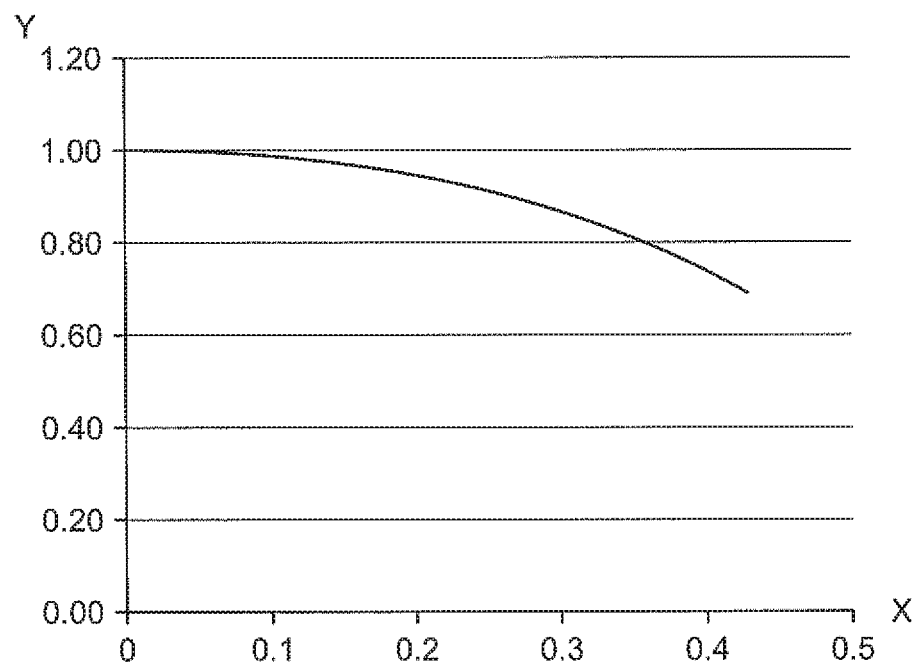
FIG. 5 is a diagram showing characteristics of a correction formula in examples 1 and 2.
Figure 6:
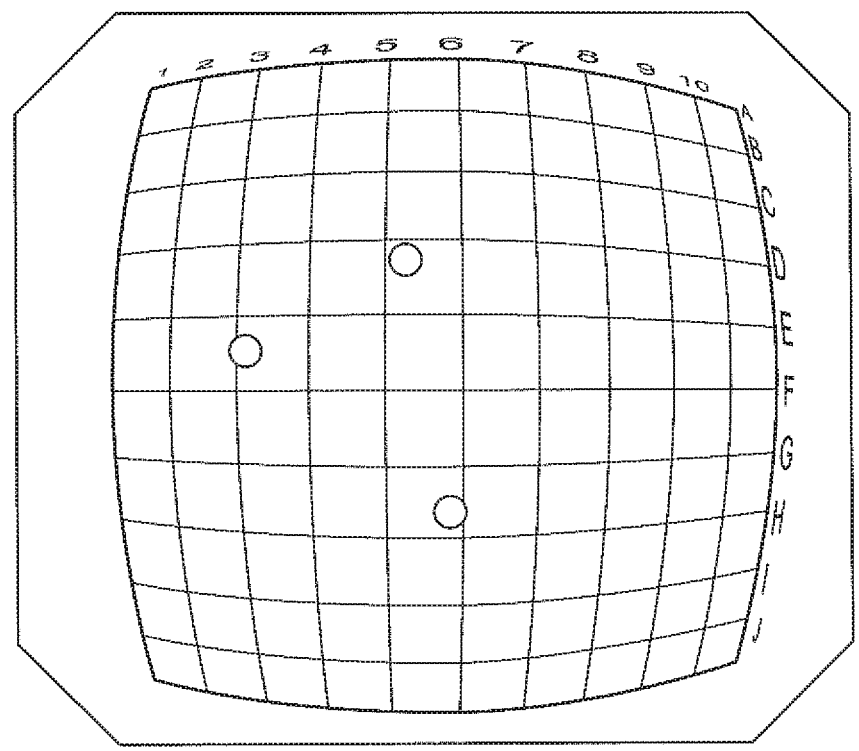
FIG. 6 is a diagram showing an observation image in a corrected state, in the example 1.

FIG. 5 shows characteristic of correction formula A. FIG. 6 shows an observation image in the examples 1 and 2. As it is evident upon comparing FIG. 4 and FIG. 6, the distortion is reduced in the examples 1 and 2. In the examples 1 and 2, an amount of reduction of distortion when the endoscope front-end is immersed into water is let to be equal.

Figure 7:
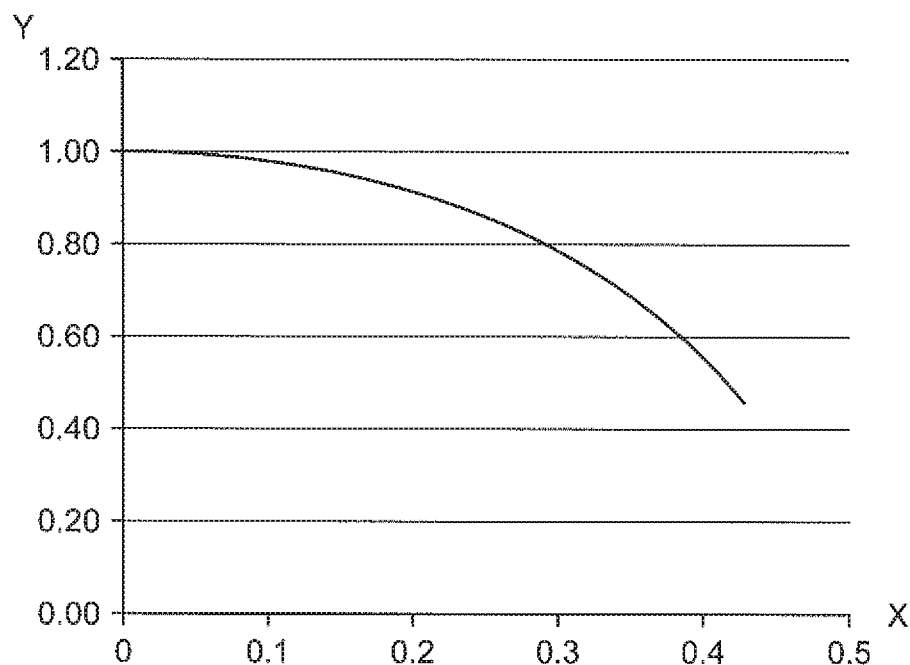
FIG. 7 is a diagram showing characteristics of correction formulae in examples 3, 4, and 5.
Figure 8:
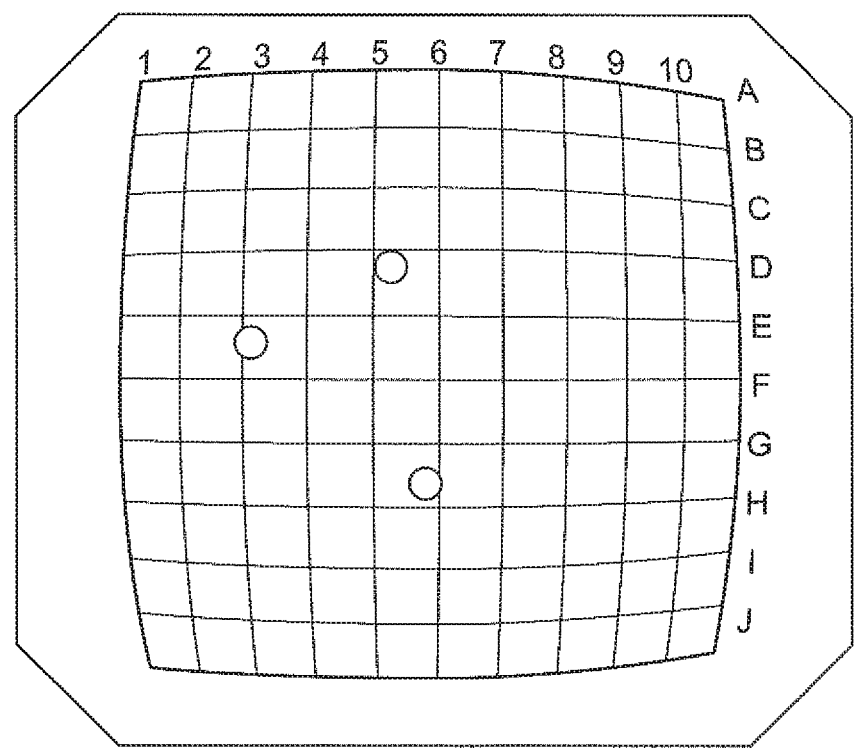
FIG. 8 is a diagram showing an observation image in a corrected state in the example 4.

FIG. 7 shows characteristic of correction formula B. FIG. 8 shows an observation image in the examples 3, 4, and 5. As it is evident upon comparing FIG. 4 and FIG. 8, the distortion is reduced substantially in the examples 3, 4, and 5.

Moreover, regarding a correction formula of image processing for reducing the distortion, it is desirable that the distortion is such that the observer has no uncomfortable feeling, and there is no problem in scenes (two scenes of in-air and in-water) that the observer uses.

In the example 1, the formula for correcting distortion is prepared such that an image is same as an image when a space between the object and the image pickup optical system (objective optical system) is filled with water (refractive index 1.33). Sometimes, the observer has to carry out in-water observation, and being used to that image, there is no uncomfortable feeling while observing that image.

Moreover, in a case of applying the correction formula, an arrangement is made such that when the in-water observation is carried out, the distortion becomes 0, and no positive reverse distortion occurs. Furthermore, coefficients of the correction formula are to be saved in the electronic endoscope 2. The image processing section 4 reads the coefficients saved, and calculates using the correction formula. By making such arrangement, it is possible to apply the most appropriate correction formula for each electronic endoscope, and also since only the coefficients are saved at the interior of the electronic endoscope, it is possible to make small a storage area which is necessary, and a cost reduction of the endoscope is also possible.

The abovementioned endoscope apparatus may satisfy the plurality of arrangement simultaneously. Making such arrangement is preferable for achieving a favorable endoscope apparatus. Moreover, combinations of the preferable arrangements are arbitrary. Regarding the conditional expressions, only an upper limit value or a lower limit value of a numerical range of a further restricted conditional expression may be restricted.

Various embodiments of the present invention were described above. However, the present invention is not restricted to the embodiments described above, and embodiments in which arrangement of the abovementioned embodiments are combined appropriately without departing from the scope of the present invention are also in the category of the present invention. For instance, in a case of applying the present invention to a zoom optical system, since an optical distortion differs for each condition, the distortion correction may be changed in accordance with each state. Moreover, the present invention may be applied to a decentered optical system, in which lenses are decentered. In this case, since the distortion of the optical system becomes rotationally asymmetric, for correcting the distortion by the image processing section 4, not a formula for rotational symmetry of expression (3), but a formula for rotational asymmetry is to be applied.

The present embodiment shows an effect that it is possible to provide an endoscope apparatus which enables both of the 2-D observation and the 3-D observation favorably.

As described heretofore, the present invention is useful for an endoscope apparatus which enables both the 2-D observation and the 3-D observation favorably.

What is claimed is:

1. An endoscope apparatus having a function of switching between a 2-D observation for a planar view and a 3-D observation for a stereoscopic view, comprising:
   an image Processor which carries out processing of reducing a distortion of an image pickup optical system for an image pickup signal achieved by an image pickup element of the endoscope apparatus at the time of the 3-D observation, wherein
   the image Processor carries out image processing that satisfies the following conditional expression (1):

$$0.1<B/A<0.8, \text{ as well as } A<0 \quad (1)$$

where,
A denotes a distortion at the maximum image height at the time of the 2-D observation, and
B denotes a distortion at the maximum image height at the time of the 3-D observation.

2. The endoscope apparatus according to claim 1, wherein the following conditional expression (2) is satisfied:

$$0.6 < D/C \leq 1 \text{ as well as } 100 \text{ degrees} < C \tag{2}$$

where,
C denotes the maximum angle of view at the time of the 2-D observation, and
D denotes the maximum angle of view at the time of the 3-D observation.

3. The endoscope apparatus according to claim 2, wherein the image Processor reduces the distortion according to the following conditional expression (3):

$$Y = E \times X^3 + F \times X^2 + G \times X + H \tag{3}$$

where,
for the maximum value of X, $0.4 < Y < 0.8$,
X denotes an image height before image processing,
Y denotes (the image height before image processing)/(an image height after image processing), and
E, F, G, and H denote coefficients.

4. The endoscope apparatus according to claim 1, wherein the following conditional expression (4) is satisfied:

$$-0.7 < B < -0.1 \tag{4}$$

where,
B denotes the distortion of the maximum image height at the time of the 3-D observation.

\* \* \* \* \*